(12) United States Patent
Crawford et al.

(10) Patent No.: US 11,786,144 B2
(45) Date of Patent: *Oct. 17, 2023

(54) METHODS OF SELECTING SURGICAL IMPLANTS AND RELATED DEVICES

(71) Applicant: GLOBUS MEDICAL, INC., Audubon, PA (US)

(72) Inventors: Neil Crawford, Chandler, AZ (US); Andrew Davison, Downingtown, PA (US); David Demski, Audubon, PA (US); Peter Govey, Ardmore, PA (US); Norbert Johnson, North Andover, MA (US); Stephanie Wolfe, Hatfield, PA (US)

(73) Assignee: Globus Medical, Inc., Audubon, PA (US)

( * ) Notice: Subject to any disclaimer, the term of this patent is extended or adjusted under 35 U.S.C. 154(b) by 108 days.

This patent is subject to a terminal disclaimer.

(21) Appl. No.: 17/462,111

(22) Filed: Aug. 31, 2021

(65) Prior Publication Data

US 2021/0386322 A1 Dec. 16, 2021

Related U.S. Application Data

(63) Continuation of application No. 15/809,110, filed on Nov. 10, 2017, now Pat. No. 11,134,862.

(51) Int. Cl.
*A61B 17/80* (2006.01)
*A61B 5/107* (2006.01)
(Continued)

(52) U.S. Cl.
CPC .............. *A61B 5/107* (2013.01); *A61B 17/80* (2013.01); *A61B 34/25* (2016.02); *G16H 30/00* (2018.01);
(Continued)

(58) Field of Classification Search
CPC .............. A61B 34/25; A61B 2034/102; A61B 2034/108; A61B 5/107; A61B 5/1072
See application file for complete search history.

(56) References Cited

U.S. PATENT DOCUMENTS 4,150,293 A 4/1979 Franke
5,246,010 A 9/1993 Gazzara et al.
(Continued)

FOREIGN PATENT DOCUMENTS

EP 1571581 A1 9/2005
JP 2006594 A 1/2006
(Continued)

OTHER PUBLICATIONS

US 8,231,638 B2, 07/2012, Swarup et al. (withdrawn)

*Primary Examiner* — Anu Ramana

(57) ABSTRACT

Methods may be provided to identify a medical implant from a plurality of medical implants to be fixed to an anatomical surface. Dimensional parameters for each of the plurality of medical implants may be provided, and dimensional parameters corresponding to the anatomical surface may be provided. The dimensional parameters for each of the plurality of medical implants may be compared with the dimensional parameters corresponding to the anatomical surface, and one of the medical implants may be selected from the plurality of medical implants based on comparing the dimensional parameters for each of the plurality of medical implants with the dimensional parameters corresponding to the anatomical surface. An identification of the medical implant selected from the plurality of medical implants may be provided through a user interface. Related devices and computer program products are also discussed.

18 Claims, 10 Drawing Sheets

(51) Int. Cl.
  *A61B 34/00* (2016.01)
  *G16H 30/00* (2018.01)
  *A61B 17/56* (2006.01)
  *A61B 34/10* (2016.01)
(52) U.S. Cl.
  CPC ... *A61B 2017/568* (2013.01); *A61B 2034/108* (2016.02); *A61F 2250/0064* (2013.01); *A61F 2250/0078* (2013.01)

(56) References Cited

U.S. PATENT DOCUMENTS

| | | | |
|---|---|---|---|
| 5,354,314 | A | 10/1994 | Hardy et al. |
| 5,397,323 | A | 3/1995 | Taylor et al. |
| 5,598,453 | A | 1/1997 | Baba et al. |
| 5,772,594 | A | 6/1998 | Barrick |
| 5,791,908 | A | 8/1998 | Gillio |
| 5,820,559 | A | 10/1998 | Ng et al. |
| 5,825,982 | A | 10/1998 | Wright et al. |
| 5,887,121 | A | 3/1999 | Funda et al. |
| 5,911,449 | A | 6/1999 | Daniele et al. |
| 5,951,475 | A | 9/1999 | Gueziec et al. |
| 5,987,960 | A | 11/1999 | Messner et al. |
| 6,012,216 | A | 1/2000 | Esteves et al. |
| 6,031,888 | A | 2/2000 | Ivan et al. |
| 6,033,415 | A | 3/2000 | Mittelstadt et al. |
| 6,080,181 | A | 6/2000 | Jensen et al. |
| 6,106,511 | A | 8/2000 | Jensen |
| 6,122,541 | A | 9/2000 | Cosman et al. |
| 6,144,875 | A | 11/2000 | Schweikard et al. |
| 6,157,853 | A | 12/2000 | Blume et al. |
| 6,167,145 | A | 12/2000 | Foley et al. |
| 6,167,292 | A | 12/2000 | Badano et al. |
| 6,201,984 | B1 | 3/2001 | Funda et al. |
| 6,203,196 | B1 | 3/2001 | Meyer et al. |
| 6,205,411 | B1 | 3/2001 | DiGioia, III et al. |
| 6,212,419 | B1 | 4/2001 | Blume et al. |
| 6,231,565 | B1 | 5/2001 | Tovey et al. |
| 6,236,875 | B1 | 5/2001 | Bucholz et al. |
| 6,246,900 | B1 | 6/2001 | Cosman et al. |
| 6,301,495 | B1 | 10/2001 | Gueziec et al. |
| 6,306,126 | B1 | 10/2001 | Montezuma |
| 6,312,435 | B1 | 11/2001 | Wallace et al. |
| 6,314,311 | B1 | 11/2001 | Williams et al. |
| 6,320,929 | B1 | 11/2001 | Von Der Haar |
| 6,322,567 | B1 | 11/2001 | Mittelstadt et al. |
| 6,325,808 | B1 | 12/2001 | Bernard et al. |
| 6,340,363 | B1 | 1/2002 | Bolger et al. |
| 6,377,011 | B1 | 4/2002 | Ben-Ur |
| 6,379,302 | B1 | 4/2002 | Kessman et al. |
| 6,402,762 | B2 | 6/2002 | Hunter et al. |
| 6,424,885 | B1 | 7/2002 | Niemeyer et al. |
| 6,447,503 | B1 | 9/2002 | Wynne et al. |
| 6,451,027 | B1 | 9/2002 | Cooper et al. |
| 6,477,400 | B1 | 11/2002 | Barrick |
| 6,484,049 | B1 | 11/2002 | Seeley et al. |
| 6,487,267 | B1 | 11/2002 | Wolter |
| 6,490,467 | B1 | 12/2002 | Bucholz et al. |
| 6,490,475 | B1 | 12/2002 | Seeley et al. |
| 6,499,488 | B1 | 12/2002 | Hunter et al. |
| 6,501,981 | B1 | 12/2002 | Schweikard et al. |
| 6,507,751 | B2 | 1/2003 | Blume et al. |
| 6,535,756 | B1 | 3/2003 | Simon et al. |
| 6,560,354 | B1 | 5/2003 | Maurer, Jr. et al. |
| 6,565,554 | B1 | 5/2003 | Niemeyer |
| 6,587,750 | B2 | 7/2003 | Gerbi et al. |
| 6,614,453 | B1 | 9/2003 | Suri et al. |
| 6,614,871 | B1 | 9/2003 | Kobiki et al. |
| 6,619,840 | B2 | 9/2003 | Rasche et al. |
| 6,636,757 | B1 | 10/2003 | Jascob et al. |
| 6,645,196 | B1 | 11/2003 | Nixon et al. |
| 6,666,579 | B2 | 12/2003 | Jensen |
| 6,669,635 | B2 | 12/2003 | Kessman et al. |
| 6,701,173 | B2 | 3/2004 | Nowinski et al. |
| 6,757,068 | B2 | 6/2004 | Foxlin |
| 6,782,287 | B2 | 8/2004 | Grzeszczuk et al. |
| 6,783,524 | B2 | 8/2004 | Anderson et al. |
| 6,786,896 | B1 | 9/2004 | Madhani et al. |
| 6,788,018 | B1 | 9/2004 | Blumenkranz |
| 6,804,581 | B2 | 10/2004 | Wang et al. |
| 6,823,207 | B1 | 11/2004 | Jensen et al. |
| 6,827,351 | B2 | 12/2004 | Graziani et al. |
| 6,837,892 | B2 | 1/2005 | Shoham |
| 6,839,612 | B2 | 1/2005 | Sanchez et al. |
| 6,856,826 | B2 | 2/2005 | Seeley et al. |
| 6,856,827 | B2 | 2/2005 | Seeley et al. |
| 6,879,880 | B2 | 4/2005 | Nowlin et al. |
| 6,892,090 | B2 | 5/2005 | Verard et al. |
| 6,920,347 | B2 | 7/2005 | Simon et al. |
| 6,922,632 | B2 | 7/2005 | Foxlin |
| 6,968,224 | B2 | 11/2005 | Kessman et al. |
| 6,978,166 | B2 | 12/2005 | Foley et al. |
| 6,988,009 | B2 | 1/2006 | Grimm et al. |
| 6,991,627 | B2 | 1/2006 | Madhani et al. |
| 6,996,487 | B2 | 2/2006 | Jutras et al. |
| 6,999,852 | B2 | 2/2006 | Green |
| 7,007,699 | B2 | 3/2006 | Martinelli et al. |
| 7,016,457 | B1 | 3/2006 | Senzig et al. |
| 7,043,961 | B2 | 5/2006 | Pandey et al. |
| 7,062,006 | B1 | 6/2006 | Pelc et al. |
| 7,063,705 | B2 | 6/2006 | Young et al. |
| 7,072,707 | B2 | 7/2006 | Galloway, Jr. et al. |
| 7,083,615 | B2 | 8/2006 | Peterson et al. |
| 7,097,640 | B2 | 8/2006 | Wang et al. |
| 7,099,428 | B2 | 8/2006 | Clinthorne et al. |
| 7,108,421 | B2 | 9/2006 | Gregerson et al. |
| 7,130,676 | B2 | 10/2006 | Barrick |
| 7,139,418 | B2 | 11/2006 | Abovitz et al. |
| 7,139,601 | B2 | 11/2006 | Bucholz et al. |
| 7,155,316 | B2 | 12/2006 | Sutherland et al. |
| 7,164,968 | B2 | 1/2007 | Treat et al. |
| 7,167,738 | B2 | 1/2007 | Schweikard et al. |
| 7,169,141 | B2 | 1/2007 | Brock et al. |
| 7,172,627 | B2 | 2/2007 | Fiere et al. |
| 7,194,120 | B2 | 3/2007 | Wicker et al. |
| 7,197,107 | B2 | 3/2007 | Arai et al. |
| 7,231,014 | B2 | 6/2007 | Levy |
| 7,231,063 | B2 | 6/2007 | Naimark et al. |
| 7,239,940 | B2 | 7/2007 | Wang et al. |
| 7,248,914 | B2 | 7/2007 | Hastings et al. |
| 7,301,648 | B2 | 11/2007 | Foxlin |
| 7,302,288 | B1 | 11/2007 | Schellenberg |
| 7,313,430 | B2 | 12/2007 | Urquhart et al. |
| 7,318,805 | B2 | 1/2008 | Schweikard et al. |
| 7,318,827 | B2 | 1/2008 | Leitner et al. |
| 7,319,897 | B2 | 1/2008 | Leitner et al. |
| 7,324,623 | B2 | 1/2008 | Heuscher et al. |
| 7,327,865 | B2 | 2/2008 | Fu et al. |
| 7,331,967 | B2 | 2/2008 | Lee et al. |
| 7,333,642 | B2 | 2/2008 | Green |
| 7,339,341 | B2 | 3/2008 | Oleynikov et al. |
| 7,366,562 | B2 | 4/2008 | Dukesherer et al. |
| 7,379,790 | B2 | 5/2008 | Toth et al. |
| 7,386,365 | B2 | 6/2008 | Nixon |
| 7,422,592 | B2 | 9/2008 | Morley et al. |
| 7,435,216 | B2 | 10/2008 | Kwon et al. |
| 7,440,793 | B2 | 10/2008 | Chauhan et al. |
| 7,460,637 | B2 | 12/2008 | Clinthorne et al. |
| 7,466,303 | B2 | 12/2008 | Yi et al. |
| 7,493,153 | B2 | 2/2009 | Ahmed et al. |
| 7,505,617 | B2 | 3/2009 | Fu et al. |
| 7,533,892 | B2 | 5/2009 | Schena et al. |
| 7,542,791 | B2 | 6/2009 | Mire et al. |
| 7,555,331 | B2 | 6/2009 | Viswanathan |
| 7,567,834 | B2 | 7/2009 | Clayton et al. |
| 7,594,912 | B2 | 9/2009 | Cooper et al. |
| 7,606,613 | B2 | 10/2009 | Simon et al. |
| 7,607,440 | B2 | 10/2009 | Coste-Maniere et al. |
| 7,623,902 | B2 | 11/2009 | Pacheco |
| 7,630,752 | B2 | 12/2009 | Viswanathan |
| 7,630,753 | B2 | 12/2009 | Simon et al. |
| 7,643,862 | B2 | 1/2010 | Schoenefeld |
| 7,660,623 | B2 | 2/2010 | Hunter et al. |
| 7,661,881 | B2 | 2/2010 | Gregerson et al. |

(56) References Cited

U.S. PATENT DOCUMENTS

| | | | |
|---|---|---|---|
| 7,683,331 | B2 | 3/2010 | Chang |
| 7,683,332 | B2 | 3/2010 | Chang |
| 7,689,320 | B2 | 3/2010 | Prisco et al. |
| 7,691,098 | B2 | 4/2010 | Wallace et al. |
| 7,702,379 | B2 | 4/2010 | Avinash et al. |
| 7,702,477 | B2 | 4/2010 | Tuemmler et al. |
| 7,711,083 | B2 | 5/2010 | Heigl et al. |
| 7,711,406 | B2 | 5/2010 | Kuhn et al. |
| 7,720,523 | B2 | 5/2010 | Omernick et al. |
| 7,725,253 | B2 | 5/2010 | Foxlin |
| 7,726,171 | B2 | 6/2010 | Langlotz et al. |
| 7,742,801 | B2 | 6/2010 | Neubauer et al. |
| 7,751,865 | B2 | 7/2010 | Jascob et al. |
| 7,760,849 | B2 | 7/2010 | Zhang |
| 7,762,825 | B2 | 7/2010 | Burbank et al. |
| 7,763,015 | B2 | 7/2010 | Cooper et al. |
| 7,787,699 | B2 | 8/2010 | Mahesh et al. |
| 7,796,728 | B2 | 9/2010 | Bergfjord |
| 7,813,838 | B2 | 10/2010 | Sommer |
| 7,818,044 | B2 | 10/2010 | Dukesherer et al. |
| 7,819,859 | B2 | 10/2010 | Prisco et al. |
| 7,824,401 | B2 | 11/2010 | Manzo et al. |
| 7,831,294 | B2 | 11/2010 | Viswanathan |
| 7,834,484 | B2 | 11/2010 | Sartor |
| 7,835,557 | B2 | 11/2010 | Kendrick et al. |
| 7,835,778 | B2 | 11/2010 | Foley et al. |
| 7,835,784 | B2 | 11/2010 | Mire et al. |
| 7,840,253 | B2 | 11/2010 | Tremblay et al. |
| 7,840,256 | B2 | 11/2010 | Lakin et al. |
| 7,843,158 | B2 | 11/2010 | Prisco |
| 7,844,320 | B2 | 11/2010 | Shahidi |
| 7,853,305 | B2 | 12/2010 | Simon et al. |
| 7,853,313 | B2 | 12/2010 | Thompson |
| 7,865,269 | B2 | 1/2011 | Prisco et al. |
| D631,966 | S | 2/2011 | Perloff et al. |
| 7,879,045 | B2 | 2/2011 | Gielen et al. |
| 7,881,767 | B2 | 2/2011 | Strommer et al. |
| 7,881,770 | B2 | 2/2011 | Melkent et al. |
| 7,886,743 | B2 | 2/2011 | Cooper et al. |
| RE42,194 | E | 3/2011 | Foley et al. |
| RE42,226 | E | 3/2011 | Foley et al. |
| 7,900,524 | B2 | 3/2011 | Calloway et al. |
| 7,907,166 | B2 | 3/2011 | Lamprecht et al. |
| 7,909,122 | B2 | 3/2011 | Schena et al. |
| 7,925,653 | B2 | 4/2011 | Saptharishi |
| 7,930,065 | B2 | 4/2011 | Larkin et al. |
| 7,935,130 | B2 | 5/2011 | Willliams |
| 7,940,999 | B2 | 5/2011 | Liao et al. |
| 7,945,012 | B2 | 5/2011 | Ye et al. |
| 7,945,021 | B2 | 5/2011 | Shapiro et al. |
| 7,953,470 | B2 | 5/2011 | Vetter et al. |
| 7,954,397 | B2 | 6/2011 | Choi et al. |
| 7,971,341 | B2 | 7/2011 | Dukesherer et al. |
| 7,974,674 | B2 | 7/2011 | Hauck et al. |
| 7,974,677 | B2 | 7/2011 | Mire et al. |
| 7,974,681 | B2 | 7/2011 | Wallace et al. |
| 7,979,157 | B2 | 7/2011 | Anvari |
| 7,983,733 | B2 | 7/2011 | Viswanathan |
| 7,988,215 | B2 | 8/2011 | Seibold |
| 7,996,110 | B2 | 8/2011 | Lipow et al. |
| 8,004,121 | B2 | 8/2011 | Sartor |
| 8,004,229 | B2 | 8/2011 | Nowlin et al. |
| 8,010,177 | B2 | 8/2011 | Csavoy et al. |
| 8,019,045 | B2 | 9/2011 | Kato |
| 8,021,310 | B2 | 9/2011 | Sanborn et al. |
| 8,035,685 | B2 | 10/2011 | Jensen |
| 8,046,054 | B2 | 10/2011 | Kim et al. |
| 8,046,057 | B2 | 10/2011 | Clarke |
| 8,052,688 | B2 | 11/2011 | Wolf, II |
| 8,054,184 | B2 | 11/2011 | Cline et al. |
| 8,054,752 | B2 | 11/2011 | Druke et al. |
| 8,057,397 | B2 | 11/2011 | Li et al. |
| 8,057,407 | B2 | 11/2011 | Martinelli et al. |
| 8,062,288 | B2 | 11/2011 | Cooper et al. |
| 8,062,375 | B2 | 11/2011 | Glerum et al. |
| 8,066,524 | B2 | 11/2011 | Burbank et al. |
| 8,072,654 | B2 | 12/2011 | Lefevere |
| 8,073,335 | B2 | 12/2011 | Labonville et al. |
| 8,079,950 | B2 | 12/2011 | Stern et al. |
| 8,086,299 | B2 | 12/2011 | Adler et al. |
| 8,092,370 | B2 | 1/2012 | Roberts et al. |
| 8,098,914 | B2 | 1/2012 | Liao et al. |
| 8,100,950 | B2 | 1/2012 | St. Clair et al. |
| 8,105,320 | B2 | 1/2012 | Manzo |
| 8,108,025 | B2 | 1/2012 | Csavoy et al. |
| 8,109,877 | B2 | 2/2012 | Moctezuma de la Barrera et al. |
| 8,112,292 | B2 | 2/2012 | Simon |
| 8,116,430 | B1 | 2/2012 | Shapiro et al. |
| 8,120,301 | B2 | 2/2012 | Goldberg et al. |
| 8,121,249 | B2 | 2/2012 | Wang et al. |
| 8,123,675 | B2 | 2/2012 | Funda et al. |
| 8,133,229 | B1 | 3/2012 | Bonutti |
| 8,142,420 | B2 | 3/2012 | Schena |
| 8,147,494 | B2 | 4/2012 | Leitner et al. |
| 8,150,494 | B2 | 4/2012 | Simon et al. |
| 8,150,497 | B2 | 4/2012 | Gielen et al. |
| 8,150,498 | B2 | 4/2012 | Gielen et al. |
| 8,165,658 | B2 | 4/2012 | Waynik et al. |
| 8,170,313 | B2 | 5/2012 | Kendrick et al. |
| 8,179,073 | B2 | 5/2012 | Farritor et al. |
| 8,182,476 | B2 | 5/2012 | Julian et al. |
| 8,184,880 | B2 | 5/2012 | Zhao et al. |
| 8,202,278 | B2 | 6/2012 | Orban, III et al. |
| 8,208,708 | B2 | 6/2012 | Homan et al. |
| 8,208,988 | B2 | 6/2012 | Jensen |
| 8,219,177 | B2 | 7/2012 | Smith et al. |
| 8,219,178 | B2 | 7/2012 | Smith et al. |
| 8,220,468 | B2 | 7/2012 | Cooper et al. |
| 8,224,024 | B2 | 7/2012 | Foxlin et al. |
| 8,224,484 | B2 | 7/2012 | Swarup et al. |
| 8,225,798 | B2 | 7/2012 | Baldwin et al. |
| 8,228,368 | B2 | 7/2012 | Zhao et al. |
| 8,231,610 | B2 | 7/2012 | Jo et al. |
| 8,263,933 | B2 | 7/2012 | Hartmann et al. |
| 8,239,001 | B2 | 8/2012 | Verard et al. |
| 8,241,271 | B2 | 8/2012 | Millman et al. |
| 8,248,413 | B2 | 8/2012 | Gattani et al. |
| 8,256,319 | B2 | 9/2012 | Cooper et al. |
| 8,271,069 | B2 | 9/2012 | Jascob et al. |
| 8,271,130 | B2 | 9/2012 | Hourtash |
| 8,281,670 | B2 | 10/2012 | Larkin et al. |
| 8,282,653 | B2 | 10/2012 | Nelson et al. |
| 8,301,226 | B2 | 10/2012 | Csavoy et al. |
| 8,311,611 | B2 | 11/2012 | Csavoy et al. |
| 8,320,991 | B2 | 11/2012 | Jascob et al. |
| 8,332,012 | B2 | 12/2012 | Kienzle, III |
| 8,333,755 | B2 | 12/2012 | Cooper et al. |
| 8,335,552 | B2 | 12/2012 | Stiles |
| 8,335,557 | B2 | 12/2012 | Maschke |
| 8,348,931 | B2 | 1/2013 | Cooper et al. |
| 8,353,963 | B2 | 1/2013 | Glerum |
| 8,358,818 | B2 | 1/2013 | Miga et al. |
| 8,359,730 | B2 | 1/2013 | Burg et al. |
| 8,374,673 | B2 | 2/2013 | Adcox et al. |
| 8,374,723 | B2 | 2/2013 | Zhao et al. |
| 8,379,791 | B2 | 2/2013 | Forthmann et al. |
| 8,386,019 | B2 | 2/2013 | Camus et al. |
| 8,392,022 | B2 | 3/2013 | Ortmaier et al. |
| 8,394,099 | B2 | 3/2013 | Patwardhan |
| 8,395,342 | B2 | 3/2013 | Prisco |
| 8,398,634 | B2 | 3/2013 | Manzo et al. |
| 8,400,094 | B2 | 3/2013 | Schena |
| 8,414,957 | B2 | 4/2013 | Enzerink et al. |
| 8,418,073 | B2 | 4/2013 | Mohr et al. |
| 8,450,694 | B2 | 5/2013 | Baviera et al. |
| 8,452,447 | B2 | 5/2013 | Nixon |
| RE44,305 | E | 6/2013 | Foley et al. |
| 8,462,911 | B2 | 6/2013 | Vesel et al. |
| 8,465,476 | B2 | 6/2013 | Rogers et al. |
| 8,465,771 | B2 | 6/2013 | Wan et al. |
| 8,467,851 | B2 | 6/2013 | Mire et al. |
| 8,467,852 | B2 | 6/2013 | Csavoy et al. |
| 8,469,947 | B2 | 6/2013 | Devengenzo et al. |
| RE44,392 | E | 7/2013 | Hynes |

(56) References Cited

U.S. PATENT DOCUMENTS

| | | |
|---|---|---|
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Isaacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | Von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0036302 A1 | 11/2001 | Miller |
| 2002/0035321 A1 | 3/2002 | Bucholz et al. |
| 2002/0059049 A1 | 8/2002 | Bradbury et al. |
| 2004/0068172 A1 | 4/2004 | Nowinski et al. |

(56) References Cited

U.S. PATENT DOCUMENTS

| | | |
|---|---|---|
| 2004/0076259 A1 | 4/2004 | Jensen et al. |
| 2004/0171924 A1 | 9/2004 | Mire et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | Von Jako |
| 2008/0109012 A1 | 5/2008 | Falco et al. |
| 2008/0144906 A1 | 6/2008 | Allred et al. |
| 2008/0161680 A1 | 7/2008 | Von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Gratacos Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2012/0310399 A1 | 12/2012 | Metzger |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |

(56) References Cited

U.S. PATENT DOCUMENTS

| | | |
|---|---|---|
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0088293 A1 | 3/2015 | Metzger |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0000569 A1 | 1/2017 | Mahfouz |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0143494 A1 | 5/2017 | Mahfouz |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |

FOREIGN PATENT DOCUMENTS

| | | |
|---|---|---|
| JP | 2006000594 A | 1/2006 |
| KR | 101147936 B1 | 2/2012 |

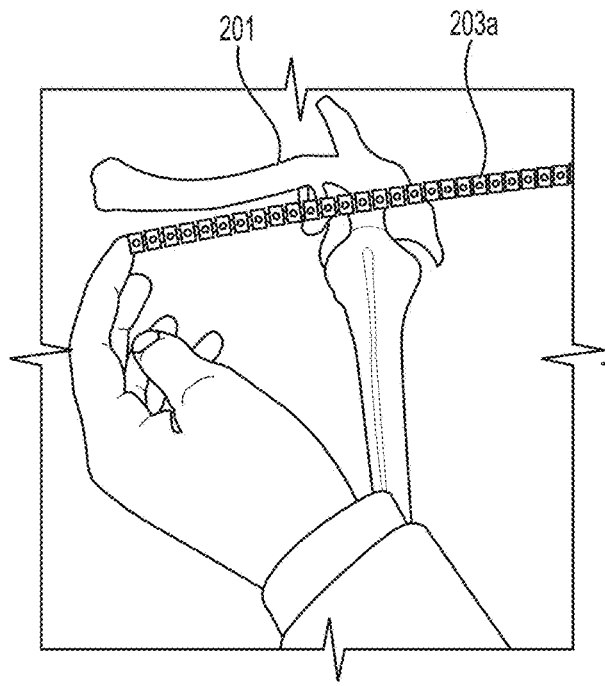 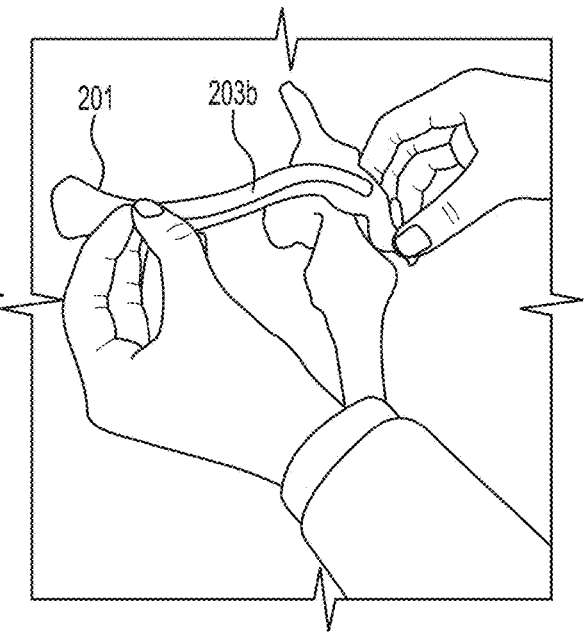
*FIG. 2A*  *FIG. 2B*
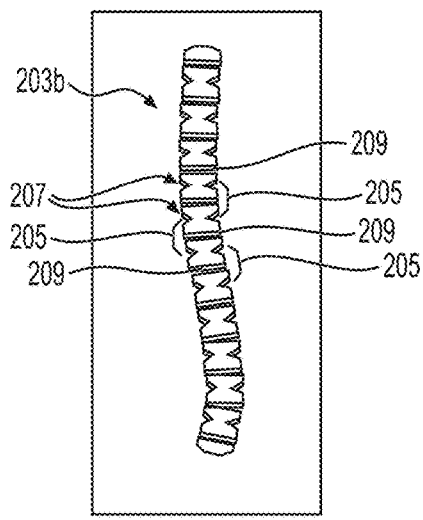 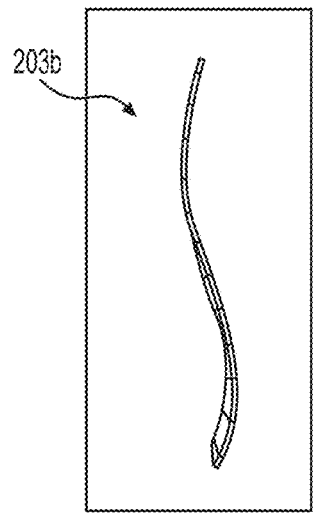
*FIG. 3A*  *FIG. 3B*

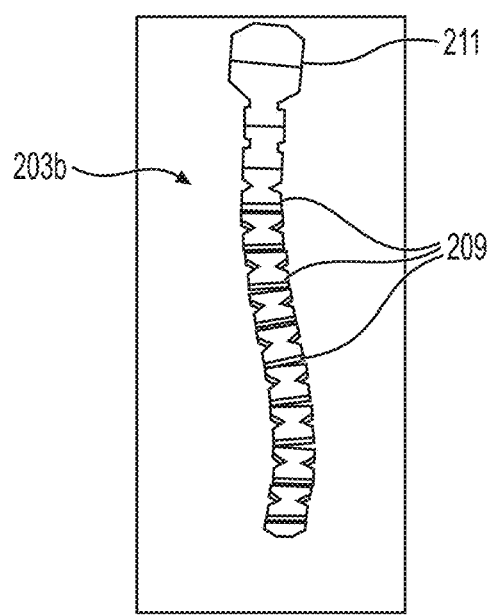 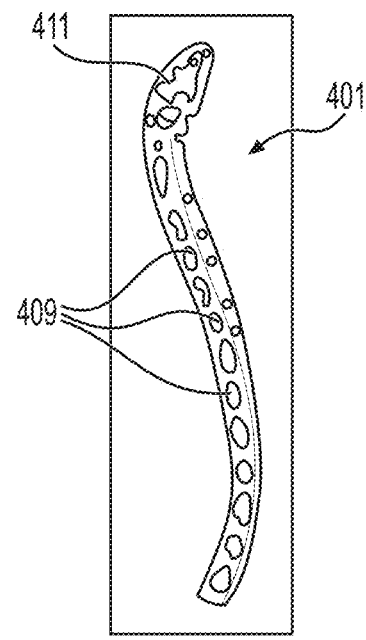
FIG. 4A  FIG. 4B
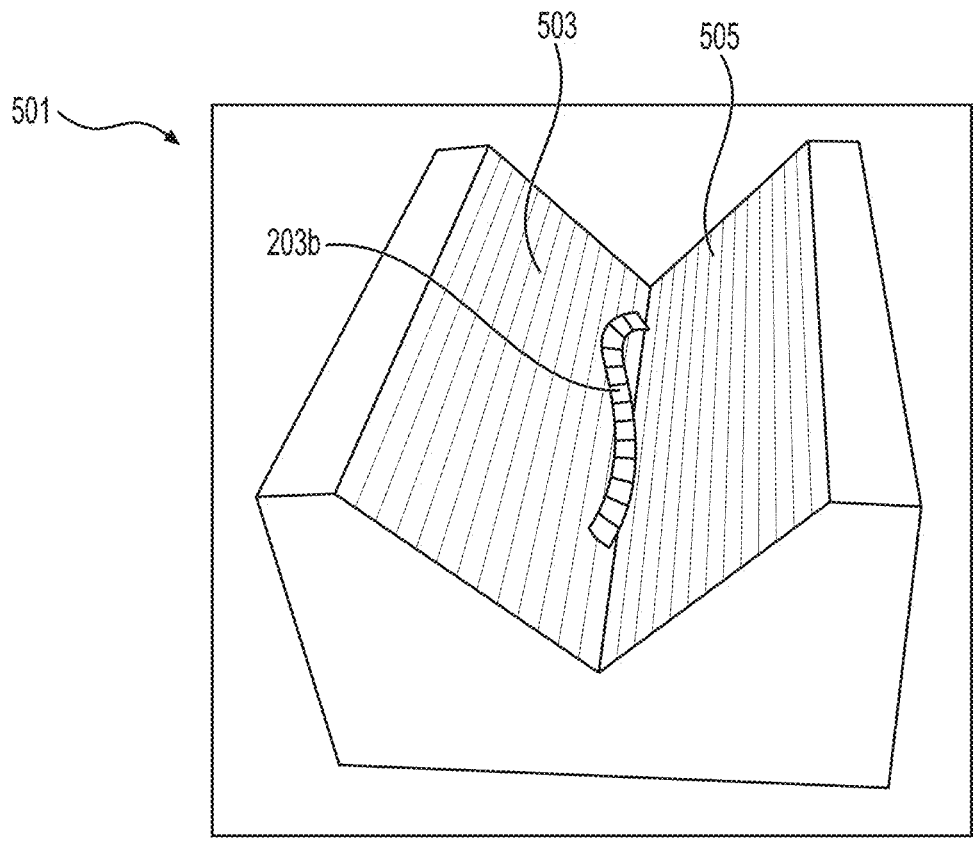
FIG. 5

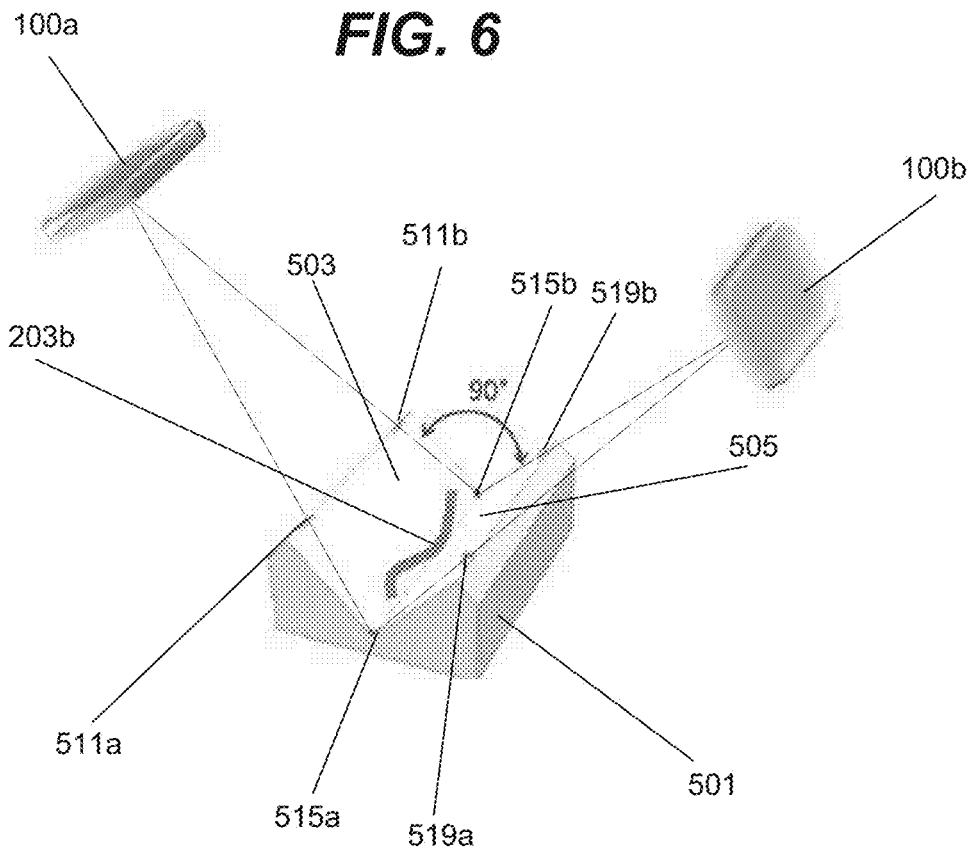
FIG. 6
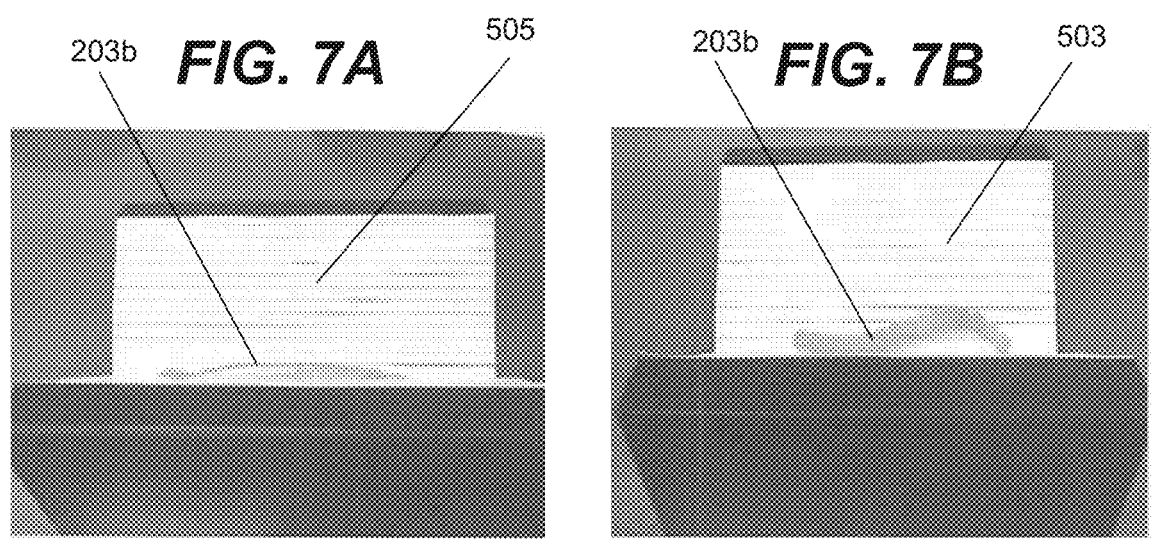
FIG. 7A  FIG. 7B

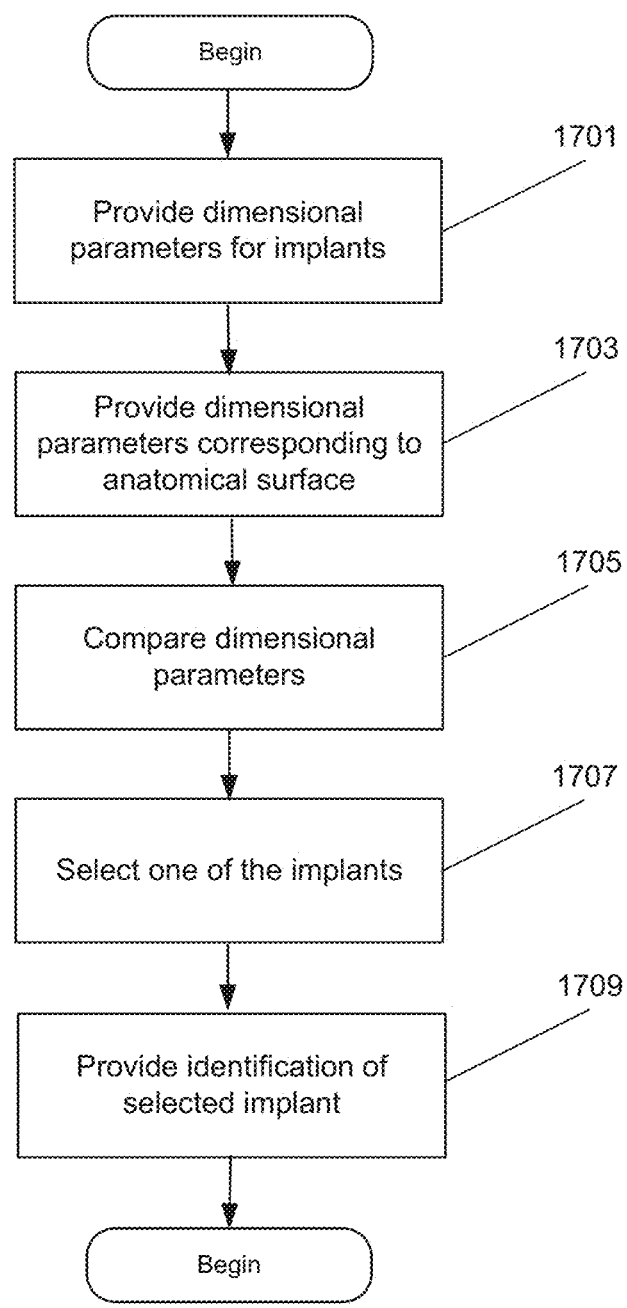

METHODS OF SELECTING SURGICAL IMPLANTS AND RELATED DEVICES

CROSS-REFERENCE TO RELATED APPLICATION(S)

The present application is a continuation application of U.S. patent application Ser. No. 15/809,110, filed on Nov. 10, 2017 (published as U.S. Patent Publication No. 2019-0142304), which is incorporated herein by reference in its entirety for all purposes.

TECHNICAL FIELD

The present disclosure relates to medical procedures and, more particular, to medical implants and related methods, devices, and computer program products.

BACKGROUND

An orthopedic implant (such as a bone plate) may be used, for example, to support a damaged bone. The implant may be fabricated from stainless steel and/or titanium alloys, and a plurality of screw holes through the implant may allow fixation to the bone using bone screws. The surgeon may thus expose the damaged bone and screw the implant to the bone.

To facilitate variations in bone sizes and/or shapes, an implant for a particular bone may be manufactured in different sizes and/or shapes. The unique anatomy and injury pattern of each individual patient may thus require selection of a properly sized and contoured implant from a set of many available sizes and contours for the same type of implant. Positive treatment outcomes may correlate with well-fitting implants.

Accordingly, the surgeon may select from a number of implant sizes/shapes during surgery to fit the bone being repaired. The selection of a particular implant may involve the surgeon visually inspecting the exposed bone surface during surgery and selecting one or more of the implants based on the visual inspection. Selecting a best-fitting implant from among many implants may thus be a time-consuming and imprecise process for the surgeon, thereby increasing a time required to perform the surgery. Moreover, the surgeon may try to fit multiple implants to the bone before selecting the final implant resulting in waste due to contamination of implants that are tried but not used.

Accordingly, there continues to exist demand for improved methods of selecting orthopedic implants.

SUMMARY

Some embodiments of the present disclosure are directed to methods to identify a medical implant from a plurality of medical implants to be fixed to an anatomical surface. Dimensional parameters for each of the plurality of medical implants may be provided, and dimensional parameters corresponding to the anatomical surface may be provided. The dimensional parameters for each of the plurality of medical implants may be compared with the dimensional parameters corresponding to the anatomical surface, and one of the medical implants may be selected from the plurality of medical implants based on comparing the dimensional parameters for each of the plurality of medical implants with the dimensional parameters corresponding to the anatomical surface. An identification of the medical implant selected from the plurality of medical implants may be provided through a user interface. Related devices and computer program products are also discussed.

Other systems, methods, and computer program products according to embodiments of the inventive subject matter will be or become apparent to one with skill in the art upon review of the following drawings and detailed description. It is intended that all such additional systems, methods, and computer program products be included within this description, be within the scope of the present inventive subject matter, and be protected by the accompanying claims. Moreover, it is intended that all embodiments disclosed herein can be implemented separately or combined in any way and/or combination.

BRIEF DESCRIPTION OF THE DRAWINGS

Other features of embodiments will be more readily understood from the following detailed description of specific embodiments thereof when read in conjunction with the accompanying drawings, in which:

FIG. 2A illustrates a template material and FIG. 2B illustrates a template on a bone according to some embodiments of inventive concepts;

FIGS. 3A and 3B illustrate orthogonal views of the template of FIG. 2B according to some embodiments of inventive concepts;

FIG. 4A illustrates a template and FIG. 4B illustrates a corresponding bone plate according to some embodiments of inventive concepts;

FIG. 5 illustrates an image cradle according to some embodiments of inventive concepts;

FIG. 6 is a diagram illustrating an image cradle using two camera positions according to some embodiments of inventive concepts;

FIGS. 7A and 7B illustrate orthogonal images of a template taken using the image cradle of FIG. 6 according to some embodiments of inventive concepts;

FIG. 17 is a flow chart illustrating operations of a selection device according to some embodiments of inventive concepts.

DETAILED DESCRIPTION

In the following detailed description, numerous specific details are set forth in order to provide a thorough understanding of embodiments of the present disclosure. However, it will be understood by those skilled in the art that the present invention may be practiced without these specific details. In other instances, well-known methods, procedures, components and circuits have not been described in detail so as not to obscure the present invention. It is intended that all embodiments disclosed herein can be implemented separately or combined in any way and/or combination.

Figure 1:
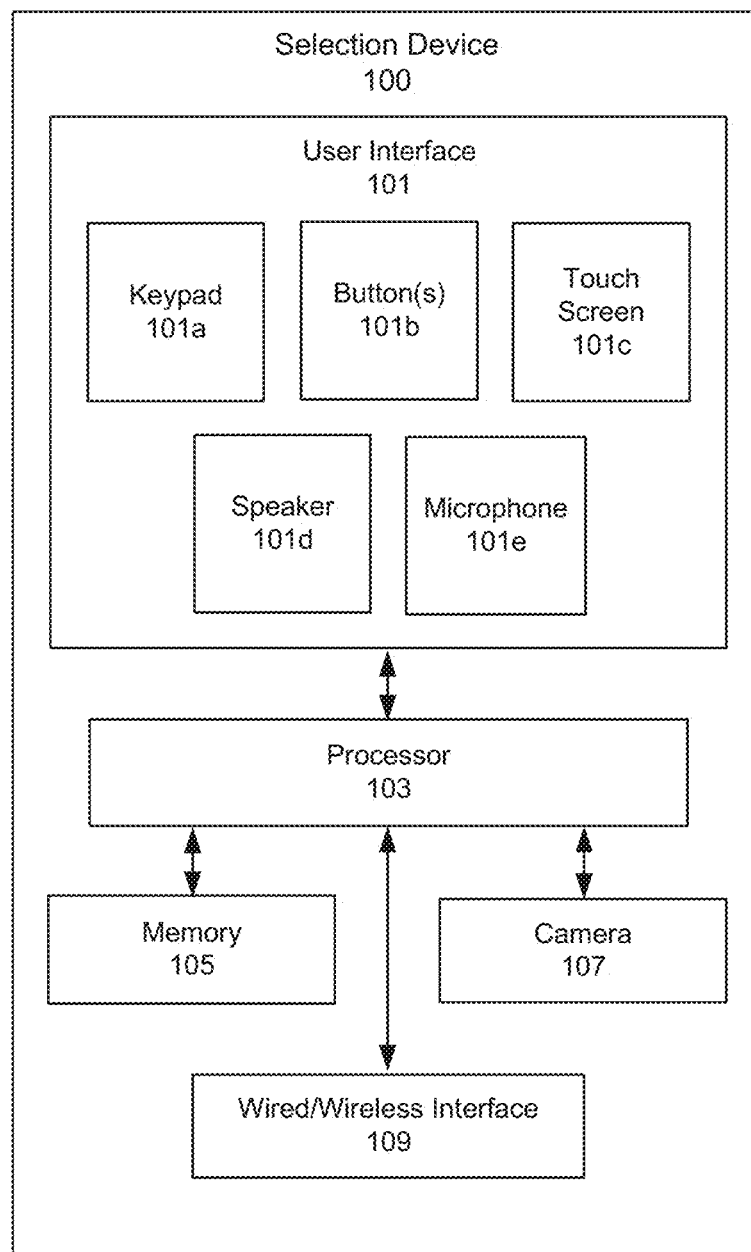
FIG. 1 is a block diagram illustrating a selection device according to some embodiments of inventive concepts.

FIG. 1 is a block diagram illustrating elements of selection device 100 configured to provide assistance in the selection of a medical implant (e.g., an orthopedic implant, such as a bone plate) according to some embodiments of inventive concepts. As shown, selection device 100 may include user interface 101, processor 103, memory 105, camera 107, and/or wired/wireless interface 109, and processor 103 may be coupled with each of user interface 101, memory 105, camera 107, and/or wired/wireless interface 109. Selection device 100 of FIG. 1, for example, may be implemented using a smartphone, a tablet computer, a laptop computer, a desktop computer, a dedicated computing device, etc., configured to perform operations to select an medical implant according to embodiments herein. Selection device 100, for example, may be a smartphone, tablet computer, laptop computer, or desktop computer running an app/software configured to perform operations discussed herein. According to some other embodiments, selection device 100 may be provided in/as a head mounted device worn by the surgeon. According to still other embodiments, selection device 100 may be integrated with other operating room equipment.

As discussed herein, operations of the selection device 100 of FIG. 1 may be performed by processor 103, user interface 101, wired/wireless interface 109, and/or camera 107. For example, processor 103 may accept data regarding the implant surface through camera 107 and/or wired/wireless interface 109, select one of a plurality of implants, and provide an identification of the selected implant through user interface 101. Moreover, modules may be stored in memory 105, and these modules may provide instructions so that when instructions of a module are executed by processor 103, processor 103 performs respective operations (e.g., operations discussed below with respect to FIG. 17). According to other embodiments, processor circuit 103 may be defined to include memory so that a separate memory is not required.

According to some embodiments, camera 107 may be used to capture images, where the images are used by processor 103 to provide/generate dimensional parameters corresponding to an anatomical surface (e.g., a bone surface) to which the implant (e.g., an orthopedic implant such as a bone plate) is to be fixed. According to some other embodiments, images or other data may be captured outside selection device 100 and received by processor 103 through wired/wireless interface 109, or dimensional parameters corresponding to the anatomical surface may be generated outside selection device 100 and received by processor 103 through wired/wireless interface 109, such that camera 107 may be omitted. Wired/wireless interface 109, for example, may include a wired interface (e.g., a Universal Serial Bus or USB port), a short range wireless interface (e.g., a BlueTooth transceiver, a WiFi transceiver, etc.), and/or a long range wireless interface (e.g., a cellular radio telephone transceiver).

As shown, user interface 101 may include one or more of a plurality of input/output devices. For example, keypad 101a, one or more buttons 101b, touch screen 101c, and/or microphone 101e may be provided to accept user input, and touch screen 101c and/or speaker 101d may provide user output (e.g., an identification of a selected medical input). According to some other embodiments, a conventional display (non-touch screen) may be used to provide user output with keypad 101a and/or button(s) 101b being used to accept user input. Camera 107, for example, may be operated responsive to user input through keypad 101a, button(s) 101b, touch screen 101c, and/or microphone 101e.

According to some embodiments of inventive concepts, methods, devices, and/or computer program products may be provided to log the unique morphology of an intended implant site (e.g., bone surface) intraoperatively and to apply best-fit algorithms to assist selection of a most suitable implant. For example, a best-fitting anatomically contoured bone plate may be selected from a plurality of bone plates according to some embodiments.

As discussed below with respect to FIGS. 2-11, a surgeon may use selection device 100 with the following operations of templating, imaging, and image analysis to select a particular implant from a plurality of implants of varying sizes and shapes/contours. While selection of a clavicle plate is discussed by way of example in the following embodiments, embodiments of inventive concepts may be applied for other medical/orthopedic implants and/or bone plates.

The surgeon may first surgically expose the site of intended plate fixation (e.g., a surface of clavicle 201), and then the surgeon may shape a malleable template to fit a 3-dimensional contour of the intended implant site. As shown in FIGS. 2A and 2B, a desired length of malleable template material 203a may be broken off (by hand) to represent a desired length of the implant, and the surgeon may shape the resulting malleable template 203b to fit a 3-dimensional contour of the exposed implant site as shown in FIG. 2B. The resulting shaped template 203b is shown in the two (substantially orthogonal) views of FIGS. 3A and 3B.

As shown in FIGS. 3A and 3B, the template 203b may have lengthwise segments 205 with lengths equal to the spacing between implant screw holes of the implant. The template material 203a may preferentially break at notches 207 between these segments, and each segment 205 may be marked with lines 209 perpendicular with respect to a trajectory of the segment. These lines 209 contrast with the template itself to facilitate image recognition. Lines 209 (or other markings) may be provided on only one of the two primary faces of the template to ensure reading of a proper orientation of the template (and not an inverted orientation). According to some embodiments, lines 209 may be provided on a face away from the bone to reduce obstruction of lines 209 due to blood or other material resulting from contact with the exposed bone. According to some other embodiments, lines 209 may be provided on a face adjacent to the bone so that the marked face of the template more closely matches the contour of the bone.

As shown in FIG. 4A, one end of template 203b may have a larger segment 211 to indicate/represent a specific end of the implant. For example, the larger segment 211 of FIG. 4A may represent a metaphyseal region 411 of bone plate 401 of FIG. 4B. This larger segment 211 of template 203b may alternatively be broken off if not wanted. In addition, lines 209 may be provided on template 203b to correspond to screw holes 409 of bone plate 401.

After shaping template 203b based on the contour and length of the implant site as shown in FIG. 2B, template 203b may be placed in imaging cradle 501 with sides 503 and 505 that are 90 degrees perpendicular (orthogonal) as shown in FIG. 5. These perpendicular surfaces 503 and 505 may have horizontal and/or vertical reference lines or other markings to facilitate image analysis by providing information about scaling and orientation of template 203b. With its V-shaped trough, imaging cradle 501 may enable complimentary imaging of template 203b at orthogonal angles, as shown in FIG. 6.

The orthogonal images of template 203b may be captured with camera 107 of selection device 100 of FIG. 1 from positions 100a and 100b as shown in FIG. 6. As discussed above, selection device 100 may be implemented using a smart phone, a tablet computer, or other similar device with on-board software. According to some other embodiments, the orthogonal images may be captured by a camera or other imaging device outside selection device 100, and the orthogonal images (or data relating thereto) may be provided through wired/wireless interface 109 of selection device 100 to processor 103. Center position and/or focal distance may be calibrated using aligning markers 511a-b, 515a-b, and 519a-b on image cradle 501. The angle of 90 degree projection images may be assisted using gyroscopic and/or accelerometer feedback that may be commonly available in smart phone devices used as selection device 100.

As shown in FIG. 6, selection device 100 including camera 107 may be held in positions 100a and 100b to take the respective images of FIGS. 7A and 7B. By aligning markers 511a and 515a and markers 511b and 515b in the image taken from position 100a and by aligning markers 519a and 515a and markers 519b and 515b in the image taken from position 100b, desired orientations of the orthogonal images may be provided. As discussed above, one camera 107 from selection device 100 (or one camera outside of selection device 100) may be used to take the orthogonal images of FIGS. 7A and 7B from positions 100a and 100b. According to some other embodiments, separate cameras may be mounted (permanently or detachably) in positions 100a and 100b to take the images of FIGS. 7A and 7B without requiring manual alignment. An image capture device, for example, may include imaging cradle 501 and two cameras that are mounted in positions 100a and 100b to capture the images of FIGS. 7A and 7B, and the resulting images (or data such as dimensional parameters relating thereto) may be provided to selection device 100 through wired/wireless interface 109.

Figure 8A:
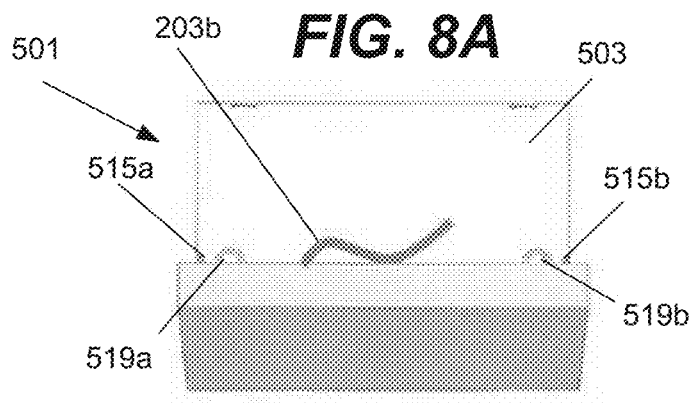
FIGS. 8A, 8B, and 8C illustrate an image cradle and alignment markings thereof according to some embodiments of inventive concepts.
Figure 8B:
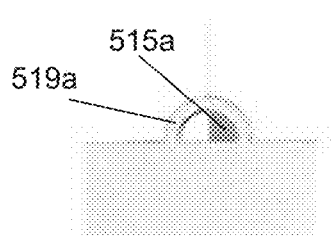
Figure 8C:
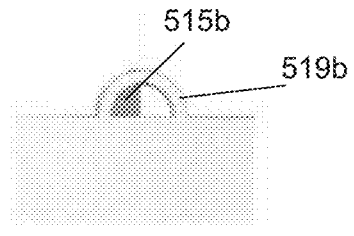

FIG. 8A shows a view of imaging cradle 501 taken from camera position 101b with alignment markers 515a-b and 519a-b. FIG. 8B shows alignment of markers 515a and 519, and FIG. 8C shows alignment of markers 515b and 519b as will occur when the camera is properly aligned at position 101b. Once the alignment of FIGS. 8B and 8C has been achieved, the image can be taken with assurance that the camera is properly positioned. If either of markers 515a and 519a or markers 515b and 519b is out of alignment after taking the image, processor 103 may reject the image and generate a request (provided through a screen/display and/or speaker of user interface 101) for the user to retake the image. According to some embodiments, processor 103 may use such visual misalignment from markers 515a, 519a, 515b, and/or 519b to adjust the image and/or data derived therefrom.

Figure 9:
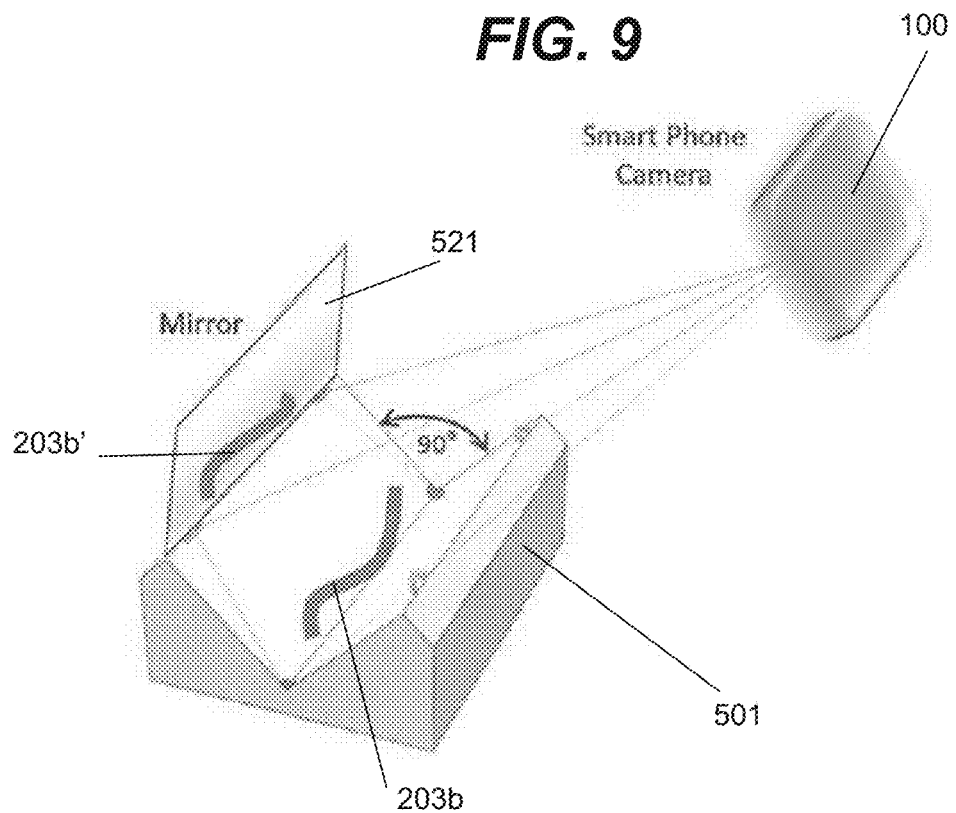
FIG. 9 is a diagram illustrating an image cradle with a mirror according to some embodiments of inventive concepts.

As shown in FIG. 9, a mirror 521 (or multiple) may be added to image cradle 501 to enable two (or more) projection angles to be captured by camera 107 of selection device 100 with one image from one angle. Mirror 521 may be a non-reversing mirror. Position and distance may again be calibrated with markers on the cradle as discussed above with respect to FIGS. 8A-C. Use of mirror 521 may allow the orthogonal images of template 203b to be captured in one photo instead of two. Here, the one image may include both a direct image of template 203b corresponding to the image of FIG. 7B and a reflection 203b' of template 203b corresponding to the image of FIG. 7A. As discussed above, camera 107 of selection device 100 may be used in FIG. 9, or a separate camera may be used with the image or data relating thereto being provided to processor 103 through wired/wireless interface 109. According to some other embodiments, a separate camera may be mounted with respect to cradle 501 to maintain a desired alignment.

In addition to a camera in a hand-held device, a head-mounted camera worn by the surgeon may be used to capture the shape of template 203b. A tracking system associated with such a head-mounted camera may provide a pose/orientation of the head-mounted camera relative to the imaging cradle 501 or holder for the implant and can provide/ensure that frames for analysis are captured at 90° or any desired angle for analysis.

In addition to or instead of a deformable template, the surgeon could place visual markers (such as reflective fiducial markers) at the anatomical site (e.g., on the exposed bone surface). Reflective fiducial markers could be tracked stereophotogrammetrically using tracking cameras, and their locations detected in 3D (3-dimensional) space. These 3D surface points could be analyzed similarly to template points and used by processor 103 to select the appropriate implant.

According to some other embodiments, surgical ink may be used wherein the surgical ink has a property/properties that cause it to selectively adhere to bone and not to surrounding soft tissue. Such ink could be detectable using visual tracking or could be radio-opaque, detectable using x-rays. Photos or radiographs of the bone with adhered ink could be processed by processor 103 to detect the bone surface contours. Selected points along the contours could be analyzed by processor 103 similarly to template points to select an appropriate implant.

Regardless of the method used to determine points on the surface of the bone where the implant is intended to rest, fitting operations discussed below may be used by processor 101.

Figure 10A:
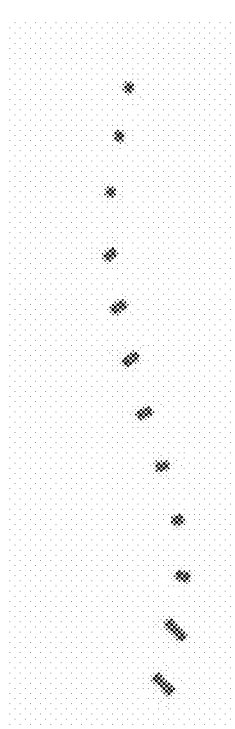
FIGS. 10A and 10B illustrate lines generated using auto-detection from different images of a template according to some embodiments of inventive concepts.
Figure 10B:
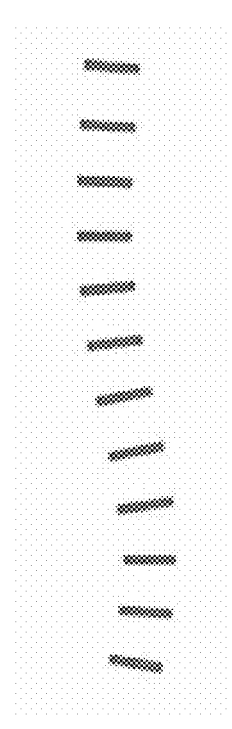
Figure 11A:
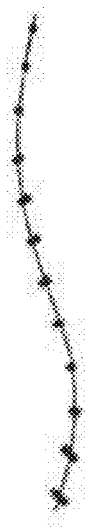
FIGS. 11A and 11B illustrate a fitting of splines using lines of FIGS. 10A and 10B according to some embodiments of inventive concepts.
Figure 11B:
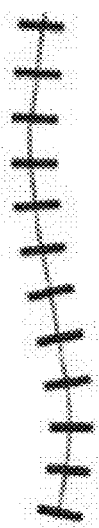

Image analysis may then be performed by processor 103 using the images of FIGS. 7A and 7B, or using the combined image resulting from FIG. 9 (or using other images or related data). In embodiments using a smartphone to implement selection device 100, a software application on the device (e.g., an Android app, an iOS app, etc.) may use operations to auto-detect the lines 209 on each segment of template 203b, in each projection (e.g., in the images of FIGS. 7A and 7B). By corresponding lines 209 with projections, processor 103 may map lines 209 to 3D space. FIG. 10A illustrates an example of processor 103 autodetecting lines 209 from the image of template 203b in FIG. 7A, and FIG. 10B illustrates an example of processor 103 autodetecting lines 209 from the image of template 203b in FIG. 7B. Processor 103 may then fit a spline through the midpoint of each line 209 as shown in FIGS. 11A and 11B.

Using the app, processor 103 may then generate prompts for questions relevant to the surgical procedure, such as anatomical placement (e.g., superior vs anterior). Processor 103, for example, may provide the prompts/questions visually through a touch screen or other display of user interface 101 and/or audibly through a speaker of user interface 101. Using the app, processor 103 may follow a best-fit algorithm to match the spline that is associated with template 203b or other method of surface geometry detection with a library or lookup table of splines corresponding to sizes/curvatures of implants available for the procedure. Using the app, processor 103 may then provide a recommendation to the user (e.g., surgeon) regarding the implant with the best-fitting spline. The recommendation may include an identification of the selected implant (e.g., a part number), a quantitative closeness of fit (e.g., 0% to 100%), and/or next-best alternatives. Using the app, processor 103 may also suggest where to bend the implant for a better fit, such as between two specific screw holes. Processor 103 could provide (on a display such as touch screen 101c or an external monitor) a graphic of the selected plate overlaid on a graphic of the template with arrows indicating where and how much to bend the plate to achieve a better fit. The recommendation(s) may be provided visually through a touch screen or other display of user interface 101 and/or audibly through a speaker of user interface 101.

Another embodiment may use the bending template to define and apply all necessary bending to a straight plate. That is, the curvature defined by the template and read from the optical or other sensing algorithm would then be applied to a straight plate either manually or automatically.

If using the system to apply bending to a straight plate through a manual process, the processor 103 could provide (on a display such as touch screen 101c or an external monitor) a graphic of the desired curvature with arrows indicating locations and magnitudes of necessary bends. Processor 103 could also show an actual size "blueprint" of the plate in its final form that could be printed or shown actual size on a monitor. The system could also assist the surgeon or technician in determining whether starting from a straight plate is a better decision than starting from a pre-bent plate and further bending the plate or back-bending it. During manual bending, the surgeon or technician could periodically hold the plate up to the template to check whether the desired curvature was achieved. Such an on-screen template might be a better visual guide for the surgeon than the physical template that was laid on bone because it may have thickness, hole spacing and general appearance more similar to the actual plate than the template itself.

If using the system to apply bending to a straight plate through an automatic process, processor 103 could electronically feed information on the locations and magnitudes of bends through wired/wireless interface to an automatic bending device. The bending device would activate a bending mechanism that could include computer-controlled rollers, clamps, and/or actuators that would apply the desired bending to the straight plate so that it best matches the template.

Use of selection device 101 and/or methods thereof may thus automate implant selection during surgery. Using such automation may reduce human error, for example, due to a surgeon overlooking and/or misjudging a best-fitting implant, and using such automation may provide quantitative evaluation to augment subjective human judgment.

Moreover, it may be difficult for a surgeon to visually assess relative fits of different implants sitting in a case, and it may be impractical to try all of them. For example, each implant that is tried but not used may be thereafter unusable due to contamination from contact to the implant site. Virtual fitting of implants according to methods/devices herein may spare unused implants from unnecessary contamination at the surgical site, thereby reducing waste. Moreover, assisted implant selection using methods/devices herein may also reduce the time of the procedure, thereby reducing time that the patient is under anesthesia, benefitting both the surgical team and patient. By improving initial selection of the implant, bending of implants to fit the patient's anatomy may be reduced. Because excessive bending of an implant may weaken the implant, a reduction in bending may reduce a risk of implant failure.

Methods, devices, and computer program products discussed herein may thus provide a combination of speed of selection and initial accuracy of fit that is not attainable using manual selection. Such speed and accuracy can reduce the time required for surgery, reduce the time that a patient is subject to anesthesia, improve a fit of the implant, and improve the ultimate patient outcome. Moreover, by providing coordinates incrementally for both the template and for the available implants, an efficiency of the comparisons may be improved thereby improving an efficiency of operations of processor 103 to improve a computer-related technology.

According to some embodiments, clavicle plate (also referred to as an implant) selection software may be provided using a Windows-based interface or a smartphone/tablet app. Image processing may include detecting curvature of template 203b (also referred to as a plate surrogate) in 2 planes and extracting the 3D shape parameters for comparison to a database of implant shapes/sizes. VTK, Qt, Open-CV and other open-source options may be used by processor 103 to detect colors and contours from photo images. Moreover, a Structured Query Language SQL database may be used to store a library of information regarding shapes, dimensions, etc., regarding the available implants. Such a database may be stored in memory 105 of selection device 100, or the database may be stored external to selection device 100 with processor 103 accessing information from the database through wired/wireless interface 109.

Upon receiving images of FIGS. 7A and 7B, for example, processor 103 may automatically process and reorient the images using alignment marks, because orientations of the images from different cameras (of different types) cannot be guaranteed and because there may be uncertainty due to variations in how the user holds the device while taking the photo(s). Alignment marks according to some embodiments are discussed above with respect to FIGS. 6, 8A-C, and 9. According to some other embodiments, alignment may be provided using marks illustrated in FIG. 12.

Figure 12:
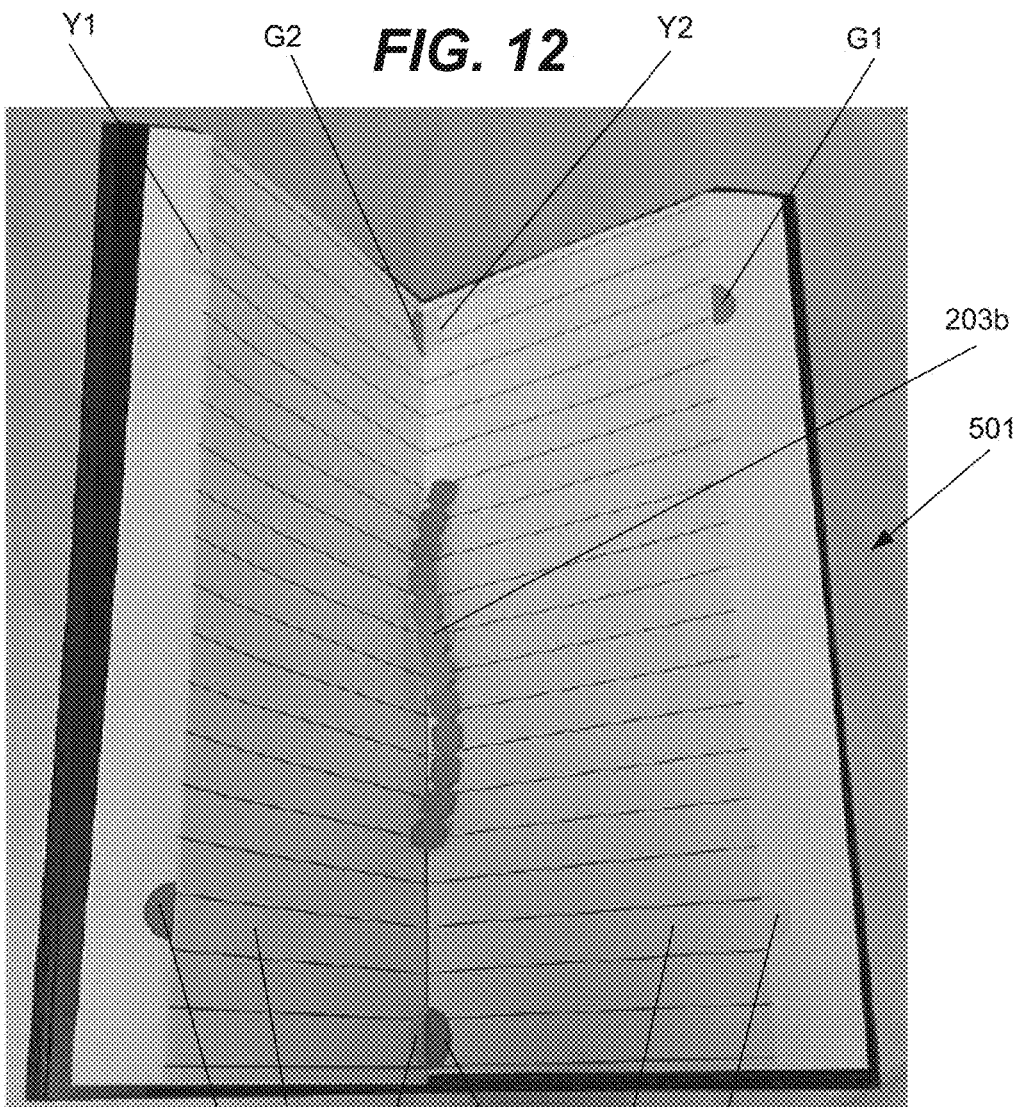
FIG. 12 illustrates a template in an image cradle including alignment markers according to some embodiments of inventive concepts.

As shown in FIG. 12, alignment marks G1 and G2 and alignment marks Y3 and Y4 may be used for one image of template 203b, and alignment marks Y1 and Y2 and alignment marks R1 and R2 may be used for another image of template 203b. These different colored alignment marks may be used to specify left-right-up-down, and these markings may be autodetected by processor 103 using Open-CV color masking operations. The alignment marks of FIG. 12 may also be used to distinguish a series of shots from one another to reduce/prevent accidental loading of duplicate shots instead of a valid pair. To distinguish the shots, one side of image cradle 501 may display yellow and green alignment marks (half circles that form circular dots when properly aligned), and the other side of image cradle 501 may display yellow and red alignment marks (half circles that form circular dots when properly aligned). As further shown in FIG. 12, lines may extend from the intersection of the two sides 503 and 505, for example, to provide scale.

Figure 13:
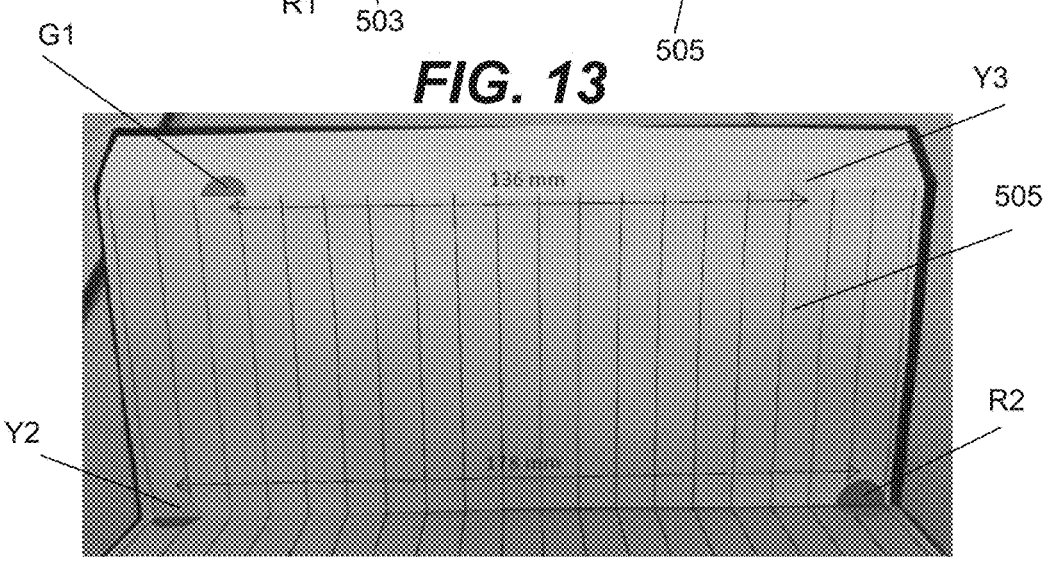
FIG. 13 illustrates different spacings of alignment markings from the image cradle of FIG. 12 according to some embodiments of inventive concepts.
Figure 14A:
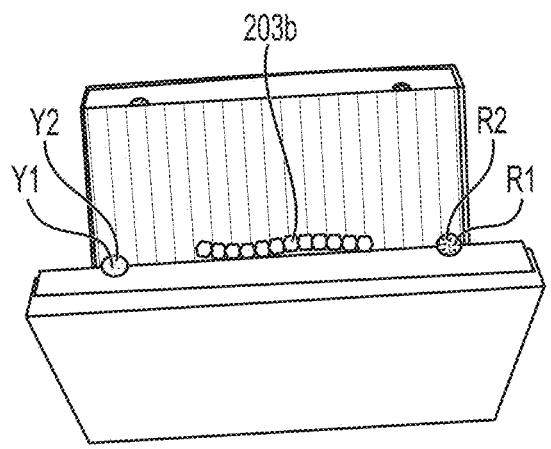
FIGS. 14A and 14B illustrate orthogonal images of a template in an image cradle using alignment markers of FIGS. 12 and 13 according to some embodiments of inventive concepts.
Figure 14B:
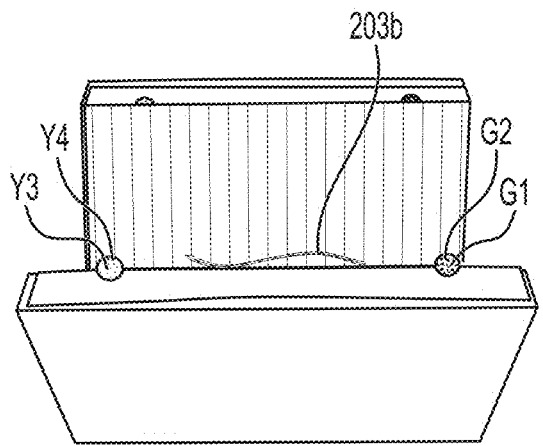

As shown in the view of FIG. 13, half circles at the intersection of the sides (e.g., Y2 and R2) may be spaced apart by 178 mm, and half circles at the top of cradle 501 (e.g., G1 and Y3) may be spaced apart by 136 mm. Moreover, half circles at the top of cradle 501 (e.g., G1 and Y3) may have a smaller diameter than half circles at the intersection of sides (e.g., Y2 and R2) because the half circles at the intersection of sides (e.g., Y2 and R2) will be further from the camera when alignment is performed and the image is taken. Alignment using this arrangement of alignment half circles may facilitate/force the user to take photos from a distance of about 35 cm from template 203b. Having this focal distance as a known value while inter-dot distance is also known may allow scaling of pixels to millimeters. Additionally, the known spacing of vertical blue lines may be 1.0 cm to provide a secondary check of the scaling. This information can be used to determine a length of template 203b. FIGS. 14A and 14B provide the resulting orthogonal images of template 203b taken using image cradle 501 with the alignment markers of FIG. 12.

Figure 15A:
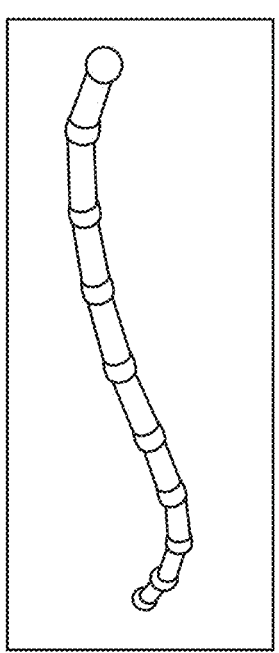
FIGS. 15A, 15B, and 15C are screenshots illustrating renderings of a spline according to some embodiments of inventive concepts.
Figure 15B:
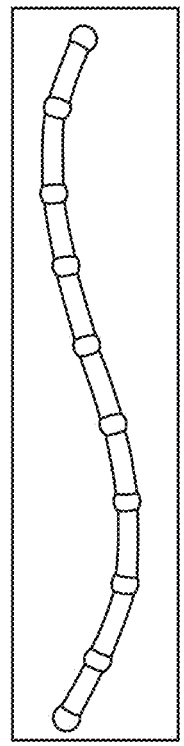
Figure 15C:
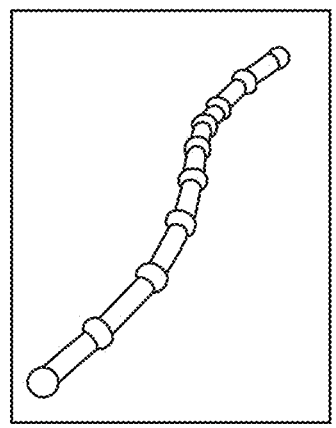

After processor 103 has processed the images of FIGS. 14A and 14B to identify segment locations, processor 103 may join the segment locations together and fit the segment locations with a spline. Processor 103 may calculate and render splines, for example, using VTK. FIGS. 15A, 15B, and 15C are screenshots showing a spline of 10 points joined together with a cylinder. According to some embodiments, it may be possible to grab each white spherical handle with a left mouse click and drag to adjust its position. It may also be possible to change the perspective view by clicking and dragging on the screen anywhere other than handle locations. In the app, processor 103 may adjust handle positions to modify a fit factor and also possibly the selection of best-fitting plate. Accordingly, it may be a useful feature to enable the user (surgeon) to proactively explore possibilities for plates/implants. For example, if the user makes the end of the plate a little more curvy, processor 103 may suggest a different plate.

According to additional embodiments, processor 103 may render images on a display of user interface 101 as flat strips joined by spheres instead of cylinders to represent actual plates. Moreover, processor 103 may only allow the user to move handles laterally on the display while keeping the longitudinal spacing between handles constant to facilitate easier comparison of the spline with a database of implant splines. Processor 103 may also use a data structure for passing spline points to code that compares the spline points to stored splines in a database.

Figure 16A:
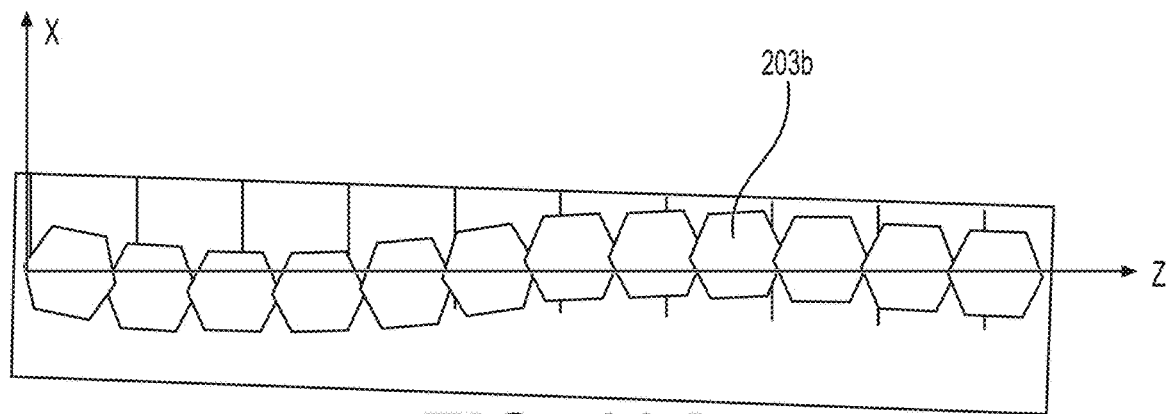
FIGS. 16A and 16B illustrate transformations of a template oriented on a z-axis according to some embodiments of inventive concepts.
Figure 16B:
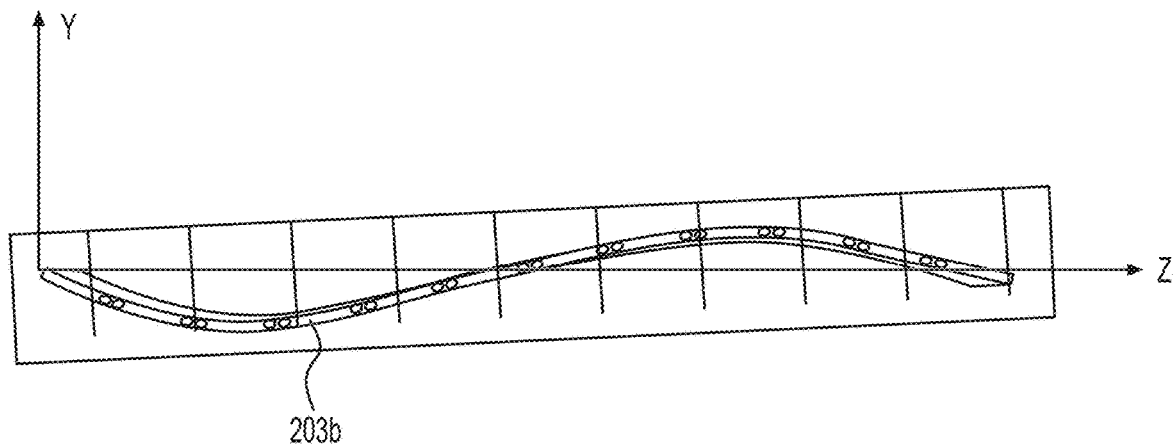

Moreover, different layouts may be provided for the database of implants. One configuration may orient the found plate shape from template 203b such that the starting end is at (xs,ys,zs)=(0,0,0) and the opposite end is at (xf,yf,zf)=(0,0,zf) as shown in FIGS. 16A and 16B. That is, processor 103 may spatially transform the shape to orient it along the z axis. Then, processor 103 may rotate the shape to place it with the flat surface of the plate parallel to the xz plane and perpendicular to the yz plane, with dorsal direction toward +y and ventral direction toward −y. This configuration is shown in FIGS. 16A and 16B.

Processor 103 may then evaluate x,y values of the template at fixed increments of z and compare these x,y values against x,y values stored in the database for the different available implants. The z increment should be fine enough to capture the curvature of the plate without having to store an excessive number of values. For example, 5 mm increments may be used. Since plates may have different lengths (in addition to different curves/contours), the number of entries evaluated and compared may depend on the desired plate length. Table 1 below shows an example for a 50 mm plate. In this example, processor 103 may query the database and measure the average vector distance from the measured 9 incremental points (i.e., points 2-10) relative to each the corresponding points stored in database entries for plates with matching length (or close to the same length). The smallest mean would be the best matching plate. This mean value would also provide a gauge of goodness of fit.

TABLE 1

Measured data for template/implants.

| Point | X | Y | Z |
|---|---|---|---|
| 1 | 0 | 0 | 0 |
| 2 | X2 | Y2 | 5 |
| 3 | X3 | Y3 | 10 |
| 4 | X4 | Y4 | 15 |
| 5 | X5 | Y5 | 20 |
| 6 | X6 | Y6 | 25 |
| 7 | X7 | Y7 | 30 |
| 8 | X8 | Y8 | 35 |
| 9 | X9 | Y9 | 40 |
| 10 | X10 | Y10 | 45 |
| 11 | 0 | 0 | 50 |

Operations of selection device 100 to identify a medical implant (e.g., a bone plate) from a plurality of medical implants will now be discussed with reference to the flow chart of FIG. 17.

At block 1701, processor 103 may provide dimensional parameters for each of the plurality of medical implants. Providing the dimensional parameters for each of the plurality of medical implants may include providing access to a stored database of the dimensional parameters that define a shape/dimensions for each of the respective medical implants of the plurality of medical implants. The stored database may be provided in memory 105 of selection device 100, or the stored database may be provided outside of selection device 100 with processor 103 accessing the stored database through wired/wireless interface 109. The stored database, for example, may include a table of points for each available implant as discussed above with respect to Table 1, such that dimensional parameters for each of the plurality of medical implants include coordinate values (e.g., x and y coordinate values) corresponding to increments along each of the medical implants (e.g., along the z-axis).

At block 1703, processor 103 may provide dimensional parameters corresponding to an anatomical surface (e.g., a surface of a bone) to which the implant is to be fixed. The dimensional parameters corresponding to the anatomical surface, for example, may include a table of points as discussed above with respect to Table 1, such that dimensional parameters corresponding to the anatomical surface include coordinate values (e.g., x and y coordinate values) corresponding to increments along the anatomical surface (e.g., along the z-axis). The dimensional parameters corresponding to the anatomical surface may be provided based on digital image data including first and second digital images that are different. Moreover, the digital image data may be taken from a template representing the anatomical surface, or the digital image data is taken from the anatomical surface (directly). Selection device 100, for example, may include camera 107 that captures digital images to be processed by processor 103 to generate the dimensional parameters. According to some other embodiments, images may be captured outside of selection device 100, received by processor 103 through wired/wireless interface 109, and processed by processor 103 to generate the dimensional parameters. According to still other embodiments, images may be captured outside selection device 100, the images may be processed outside of selection device 100 to generate the dimensional parameters, and the dimensional parameters may be received by processor 103 through wired/wireless interface 109.

At block 1705, processor 103 may compare the dimensional parameters for each of the plurality of medical implants with the dimensional parameters corresponding to the anatomical surface. For example, processor 103 may compare coordinate values (e.g., x-y coordinate values taken at increments along a z-axis) corresponding to the plurality of medical implants with coordinate values (e.g., x-y coordinate values taken at increments along a z-axis) corresponding to the anatomical surface. For such a comparison, processor 103 may determine differences between the coordinate values corresponding to the anatomical surface and respective ones of the coordinate values corresponding to each of the plurality of medical implants.

At block 1707, processor 103 may select one of the medical implants from the plurality of medical implants based on comparing the dimensional parameters for each of the plurality of medical implants with the dimensional parameters corresponding to the anatomical surface. Processor 103, for example, may select the one of the medical implants having a least average difference between the coordinate values corresponding to the anatomical surface and the coordinate values corresponding to the one of the medical implants that is selected.

At block 1709, processor 103 may provide an identification of the medical implant selected from the plurality of medical implants through user interface 101. The identification of the selected medical implant, for example, may be provided visually through a display (e.g., touch screen 101c) of user interface 101 and/or audibly through speaker 101d of user interface 101. The identification may include a name, a part number, a size, etc. In addition, processor 101 may provide additional information (visually or audibly), such as a recommended location to bend the selected implant.

As discussed above according to some embodiments, the dimensional parameters corresponding to the anatomical surface may be provided at block 1703 based on digital image data including first and second digital images that are different, with the first and second digital images being taken from template 203b representing the anatomical surface as shown, for example, in FIGS. 14A and 14B.

The first and second digital images, for example, may be taken of template 203b in image cradle 501 that includes first alignment markers (Y1, Y2, R1, and R2) for the first digital image and second alignment markers (Y3, Y4, G1, and G2) for the second digital image as discussed above, for example, with respect to FIGS. 12, 13, 14A, and 14B. Based on the images of FIGS. 14A and 14B, processor 103 may provide the dimensional parameters corresponding to the anatomical surface at block 1703 responsive to verifying alignment of the first digital image of FIG. 14A based on the first alignment markers (Y1, Y2, R1, and R2) and responsive to verifying alignment of the second digital image of FIG. 14B based on the second alignment markers (Y3, Y4, G1, and G2).

As discussed above, the first and second digital images of FIGS. 14A and 14B may be taken of template 203b in cradle 501 that includes first alignment markers (Y1, Y2, R1, and R2) for the first digital image and second alignment markers (Y3, Y4, G1, and G2) for the second digital image. At block 1703, processor 103 may use alignment markers for a digital image to determine alignment/misalignment of the image and either accept an image that is aligned, or reject an image that is misaligned and request that the user (surgeon) retake the rejected image. Processor 103, for example, may provide the dimensional parameters corresponding to the anatomical surface at block 1703 using the following operations. Responsive to first user input, a first version of the first digital image of FIG. 14A may be captured through camera 107 including template 203b in cradle 501 with first alignment markers (Y1, Y2, R1, and R2). Responsive to detecting misalignment of the first alignment markers in the first version of the first digital image of FIG. 14A, processor 103 may provide an instruction to retake the first digital image of FIG. 14A through the user interface 101 (e.g., a visual instruction through a display and/or an audible instruction through a speaker). Responsive to second user input after providing the instruction, a second version of the first digital image of FIG. 14A may be captured through camera 107 including template 203b in cradle 501 with the first alignment markers. Responsive to third user input, the second digital image of FIG. 14B may be captured through camera 107 including template 203b in cradle 501 with the second alignment markers. Responsive to the second version of the first digital image of FIG. 14A being aligned based on alignment markers (Y1, Y2, R1, and R2) and the second digital image of FIG. 14B being aligned based on alignment markers (Y3, Y4, G1, and G2), processor 103 may provide the dimensional parameters corresponding to the anatomical surface based on the second version of the first digital image and the second digital image. Either image may be rejected any number of times until each image is captured with proper alignment.

As discussed above, the first and second digital images of FIGS. 14A and 14B may be taken of template 203b in cradle 501 that includes first alignment markers (Y1, Y2, R1, and R2) for the first digital image and second alignment markers (Y3, Y4, G1, and G2) for the second digital image. Processor 103 may provide the dimensional parameters corresponding to the anatomical surface based on the at least one of the first alignment markers and/or the second alignment markers. Processor 103, for example, may use an alignment/misalignment of the alignment markers to determine a camera distance from cradle/template 501/203b, a camera angle relative to cradle/template 501/203b, and/or other information that may be used to determine dimensional parameters corresponding to the anatomical surface.

According to some other embodiments, processor 103 may the dimensional parameters corresponding to the anatomical surface based on digital image data including first and second digital images that are different, wherein the first and second digital images are taken from the anatomical surface (directly). Such images may be taken either before or during the operation, and the digital image data may include at least one of x-ray image data, computed tomography image data, ultrasound image data, magnetic resonance image data, and/or photographic image data.

According to some embodiments, providing dimensional parameters corresponding to the anatomical surface at block 1703 may include providing a curve (e.g., a spline) to represent a shape of the anatomical surface, and selecting at block 1707 may include selecting the one of the medical implants to match the shape of the anatomical surface based on the curve.

Further Definitions and Embodiments are discussed below.

In the above-description of various embodiments of the present disclosure, aspects of the present disclosure may be illustrated and described herein in any of a number of patentable classes or contexts including any new and useful process, machine, manufacture, or composition of matter, or any new and useful improvement thereof. Accordingly, aspects of the present disclosure may be implemented in entirely hardware, entirely software (including firmware, resident software, micro-code, etc.) or combining software and hardware implementation that may all generally be referred to herein as a "circuit," "module," "component," or "system." Furthermore, aspects of the present disclosure may take the form of a computer program product comprising one or more computer readable media having computer readable program code embodied thereon.

Any combination of one or more computer readable media may be used. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks.

These computer program instructions may also be stored in a computer readable medium that when executed can direct a computer processor, other programmable data processing apparatus, or other devices to function in a particular manner, such that the instructions when stored in the computer readable medium produce an article of manufacture including instructions which when executed, cause a computer processor to implement the function/act specified in the flowchart and/or block diagram block or blocks. The computer program instructions may also be loaded onto a computer processor, other programmable instruction execution apparatus, or other devices to cause a series of operational steps to be performed on the computer, other programmable apparatuses or other devices to produce a computer implemented process such that the instructions which execute on the computer processor or other programmable apparatus provide processes for implementing the functions/acts specified in the flowchart and/or block diagram block or blocks.

It is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus a first element/operation in some embodiments could be termed a second element/operation in other embodiments without departing from the teachings of present inventive concepts. The same reference numerals or the same reference designators denote the same or similar elements throughout the specification.

The flowchart and block diagrams in the figures illustrate the architecture, functionality, and operation of possible implementations of systems, methods, and computer program products according to various aspects of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular aspects only and is not intended to be limiting of the disclosure. As used herein, the singular forms "a", "an" and "the" are intended to include the plural forms as well, unless the context clearly indicates otherwise. It will be further understood that the terms "comprise", "comprising", "comprises", "include", "including", "includes", "have", "has", "having", or variants thereof are open-ended, and include one or more stated features, integers, elements, steps, components or functions but do not preclude the presence or addition of one or more other features, integers, elements, steps, components, functions or groups thereof. As used herein, the term "and/or" includes any and all combinations of one or more of the associated listed items. Like reference numbers signify like elements throughout the description of the figures.

The corresponding structures, materials, acts, and equivalents of any means or step plus function elements in the claims below are intended to include any disclosed structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The aspects of the disclosure herein were chosen and described in order to best explain principles of the disclosure and practical applications, and to enable others of ordinary skill in the art to understand the disclosure with various modifications as are suited to the particular use contemplated.

Many variations and modifications can be made to the embodiments without substantially departing from the principles of the present inventive concepts. All such variations and modifications are intended to be included herein within the scope of present inventive concepts. Accordingly, the above disclosed subject matter is to be considered illustrative, and not restrictive, and the examples of embodiments are intended to cover all such modifications, enhancements, and other embodiments, which fall within the spirit and scope of present inventive concepts. Thus, to the maximum extent allowed by law, the scope of present inventive concepts are to be determined by the broadest permissible interpretation of the present disclosure including the following claims and their equivalents, and shall not be restricted or limited by the foregoing detailed description.

The invention claimed is:

1. A system configured to identify a medical implant from a plurality of medical implants to be fixed to an anatomical surface, the system comprising:
    a processor;
    a memory coupled with the processor and comprising computer readable program code embodied in the memory that when executed by the processor causes the processor to perform operations comprising:
        receiving dimensional parameters corresponding to the anatomical surface,
        comparing the received dimensional parameters corresponding to the anatomical surface against stored dimensional parameters for the plurality of medical implants;
        selecting one of the medical implants from the plurality of medical implants based on the comparison; and
        providing an identification of the medical implant selected from the plurality of medical implants.

2. The system of claim 1, further comprising:
    a user interface coupled with the processor, wherein providing the identification comprises providing the identification as at least one of a visual output through a display of the user interface and/or an audio output through a speaker of the user interface.

3. The system of claim 2, wherein receiving dimensional parameters corresponding to the anatomical surface comprises receiving a curve to represent a shape of the anatomical surface, and wherein selecting comprises selecting the one of the medical implants to match the shape of the anatomical surface based on the curve.

4. The system of claim 1, further comprising:
    a camera coupled with the processor, wherein receiving the dimensional parameters corresponding to the anatomical surface comprises providing the dimensional parameters corresponding to the anatomical surface based on digital image data including first and second digital images received at the processor through the camera, and wherein the first and second digital images are different.

5. The system of claim 1, wherein the stored dimensional parameters for each of the plurality of medical implants includes a shape for each of the respective medical implants of the plurality of medical implants.

6. The system of claim 1, wherein the stored dimensional parameters for each of the plurality of medical implants include coordinate values corresponding to x-y coordinate values taken at increments along a z-axis of each of the medical implants, wherein receiving the dimensional parameters corresponding to the anatomical surface comprises providing coordinate values corresponding to increments along the anatomical surface, and wherein comparing comprises comparing the coordinate values corresponding to the plurality of medical implants with the coordinate values corresponding to the anatomical surface.

7. The system of claim 6, wherein comparing comprises determining differences between the coordinate values corresponding to the anatomical surface and respective ones of the coordinate values corresponding to each of the plurality of medical implants, and wherein selecting comprises selecting the one of the medical implants having a least average difference between the coordinate values corresponding to the anatomical surface and the coordinate values corresponding to the one of the medical implants that is selected.

8. The system of claim 1, wherein receiving the dimensional parameters corresponding to the anatomical surface comprises providing receiving the dimensional parameters corresponding to the anatomical surface based on digital image data including first and second digital images that are different.

9. The system of claim 8, wherein the digital image data is taken from a template representing the anatomical surface.

10. The system of claim 9, wherein the first and second digital images are taken of the template in a cradle that includes first alignment markers for the first digital image and second alignment markers for the second digital image, and wherein receiving the dimensional parameters corresponding to the anatomical surface comprises receiving the dimensional parameters corresponding to the anatomical surface based on the first and second digital images responsive to verifying alignment of the first digital image based on the first alignment markers and responsive to verifying alignment of the second digital image based on the second alignment markers.

11. The system of claim 9, further comprising a user interface coupled to the processor, and wherein the first and second images are taken of the template in a cradle including first alignment markers for the first digital image and second alignment markers for the second digital image, wherein receiving the dimensional parameters corresponding to the anatomical surface comprises:
responsive to first user input to the user interface, capturing a first version of the first digital image including the template in the cradle with the first alignment markers,
responsive to misalignment of the first alignment markers in the first version of the first digital image, providing an instruction to retake the first digital image through the user interface,
responsive to second user input to the user interface, after providing the instruction, capturing a second version of the first digital image including the template in the cradle with the first alignment markers,
responsive to third user input to the user interface, capturing the second digital image including the template in the cradle with the second alignment markers, and
receiving the dimensional parameters corresponding to the anatomical surface based on the second version of the first digital image and the second digital image.

12. The system of claim 9, wherein the first and second digital images are taken of the template in a cradle that includes first alignment markers for the first digital image and second alignment markers for the second digital image, and wherein receiving the dimensional parameters corresponding to the anatomical surface comprises receiving the dimensional parameters corresponding to the anatomical surface based on the at least one of the first alignment markers and/or the second alignment markers.

13. The system of claim 8, wherein the digital image data is taken from the anatomical surface.

14. The system of claim 13, wherein the digital image data comprises at least one of x-ray image data, computed tomography image data, ultrasound image data, magnetic resonance image data, and/or photographic image data.

15. The system of claim 1, wherein the anatomical surface is a surface of a bone.

16. A system configured to identify a medical implant from a plurality of medical implants to be fixed to an anatomical surface, the system comprising:
a processor;
a memory coupled with the processor and comprising computer readable program code embodied in the memory that when executed by the processor causes the processor to perform operations comprising:
receiving a three dimensional contour of the anatomical surface;
comparing the received three dimensional contour of the anatomical surface of the particular patient against a stored three dimensional contour of a plurality of bone plate implants for optimal fit, the stored three dimensional contour including a shape of the bone plate implant;
selecting one of the bone plate implants from the plurality of bone plate implants based on the comparison of the optimal fit; and
providing an identification of the selected bone plate implant through a user interface.

17. The system of claim 16, further comprising:
a user interface coupled with the processor, wherein providing the identification comprises providing the identification as at least one of a visual output through a display of the user interface and/or an audio output through a speaker of the user interface.

18. The system of claim 16, further comprising:
a camera coupled with the processor.

* * * * *